(12) United States Patent
Shimuta (10) Patent No.: US 11,432,730 B2
(45) Date of Patent: Sep. 6, 2022

(54) BIOSENSOR (71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 471 days.

(21) Appl. No.: 16/566,115

(22) Filed: Sep. 10, 2019

(65) Prior Publication Data
US 2020/0000352 A1 Jan. 2, 2020

Related U.S. Application Data (63) Continuation of application No. PCT/JP2018/010707, filed on Mar. 19, 2018.

(30) Foreign Application Priority Data

Mar. 31, 2017 (JP) .............................. JP2017-070226

(51) Int. Cl.
A61B 5/024 (2006.01)
H05K 1/02 (2006.01)
A61B 5/00 (2006.01)

(52) U.S. Cl.
CPC ........ *A61B 5/02427* (2013.01); *H05K 1/0274* (2013.01); *A61B 5/6826* (2013.01);
(Continued)

(58) Field of Classification Search
CPC .... A61B 2560/0425; A61B 2560/0431; A61B 2562/166; A61B 2562/185;
(Continued)

(56) References Cited

U.S. PATENT DOCUMENTS 6,062,089 A 5/2000 Ichihashi
6,528,779 B1 * 3/2003 Franz .................. G01D 5/38
250/237 G
(Continued)

FOREIGN PATENT DOCUMENTS

CN 102946796 A 2/2013
JP 2006288619 A 10/2006
(Continued)

OTHER PUBLICATIONS

International Search Report issued in PCT/JP2018/010707, dated Jun. 19, 2018.
(Continued)

*Primary Examiner* — Jonathan T Kuo
(74) *Attorney, Agent, or Firm* — ArentFox Schiff LLP (57) ABSTRACT A photoelectric pulse sensor includes a light emitting device and a light receiving device disposed on a main surface of a circuit board with a predetermined distance apart from each other. A housing is provided to which the circuit board is attached and including a pair of openings respectively corresponding to the light emitting and receiving devices, with the housing including a light shield disposed at least between the pair of openings. The light shield includes a light shield member that is disposed on a surface of the housing facing the circuit board. The light shield member has a light shielding characteristics and flexibility. The light shield member is deformed by coming into contact with the circuit board when the circuit board is attached to the housing.

22 Claims, 5 Drawing Sheets (52) U.S. Cl.
 CPC ............... *A61B 2560/0425* (2013.01); *A61B 2560/0431* (2013.01); *A61B 2562/166* (2013.01); *H05K 2201/10151* (2013.01)

(58) Field of Classification Search
 CPC .............. A61B 5/02427; A61B 5/6826; A61B 5/02–0295; H05K 1/0274; H05K 1/18; H05K 2201/0999; H05K 2201/10121; H05K 2201/10151
 See application file for complete search history.

(56) References Cited

U.S. PATENT DOCUMENTS

| | | |
|---|---|---|
| 2007/0030154 A1 | 2/2007 | Aiki et al. |
| 2014/0088396 A1 | 3/2014 | Shimuta |
| 2014/0163342 A1* | 6/2014 | Shimuta ............. A61B 5/14552 600/323 |
| 2016/0058312 A1 | 3/2016 | Han et al. |
| 2017/0172476 A1* | 6/2017 | Schilthuizen .......... A61B 5/681 |
| 2019/0086331 A1 | 3/2019 | Han et al. |

FOREIGN PATENT DOCUMENTS

| | | |
|---|---|---|
| JP | 2016052503 A | 4/2016 |
| JP | 2016123714 A | 7/2016 |
| WO | 2011162000 A1 | 12/2011 |
| WO | 2012165064 A1 | 12/2012 |
| WO | 2013027359 A1 | 2/2013 |

OTHER PUBLICATIONS

Chinese Office Action issued for Chinese Application No. 20188002297.8, dated Aug. 23, 2021.

* cited by examiner

[BEFORE ATTACHMENT OF SUBSTRATE]

[AFTER ATTACHMENT OF SUBSTRATE]

BIOSENSOR

CROSS REFERENCE TO RELATED APPLICATIONS

The present application is a continuation of PCT/JP2018/010707 filed Mar. 19, 2018, which claims priority to Japanese Patent Application No. 2017-070226, filed Mar. 31, 2017, the entire contents of each of which are incorporated herein by reference.

TECHNICAL FIELD

The present invention relates to a biosensor that acquires biosignals.

BACKGROUND

In recent years, health management, maintenance, and/or promotion has been increasingly attracting the attention of many people. Many people desire to more easily acquire vital signs such as the pulse or heartbeat. Existing biosensors known thus far acquire, in the form of a photoelectric pulse signal, a change of the intensity of light that has passed through or that has been reflected off a living body such as fingers using the characteristics of the hemoglobin in the blood absorbing visible light to infrared light.

For example, Patent Document 1 (identified below) discloses a wristband sensor node. This sensor node includes a pair of infrared light emitting diodes and a phototransistor, which form a pulse sensor and are linearly disposed on a substrate. These infrared light emitting diodes and the phototransistor are disposed to oppose the skin through an opening in a casing. The substrate is supported on the back surface of a motherboard.

Moreover, Patent Document 2 (also identified below) discloses a photoplethysmograph ("PPG") device that includes one or more light emitters and one or more light sensors to generate multiple light paths for measuring a PPG signal of a user. In this photoplethysmograph device, the light emitters and the light sensors are mounted on a component mounting plane. Between the light emitters and the light sensors, an optical isolation is disposed. The optical isolation is made of, for example, an opaque material to reduce parasitic DC light.

Patent Document 1: Japanese Unexamined Patent Application Publication No. 2006-288619.

Patent Document 2: Japanese Unexamined Patent Application Publication No. 2016-52503.

The sensor node according to Patent Document 1 is designed to block, with the casing, stray light that is directly incident on a phototransistor from the infrared light emitting diodes without passing through a living body. However, even a slight gap formed between the casing and the substrate causes stray light, which may disable the light sensor.

In the photoplethysmograph device described in Patent Document 2, on the other hand, the optical isolation is disposed between the light emitters and the light sensors. This structure prevents stray light from passing through a gap between the casing and the substrate, unlike in the above sensor node according to Patent Document 1. However, when, for example, the housing bears external pressure during measurement or in other occasions, the optical isolation with insufficient stiffness may be deformed with the pressure. Here, the pressure is exerted on the component mounting plane with the optical isolation interposed therebetween, and the component mounting plane may be distorted with the pressure, and the mounted components may cause connection errors or other defects.

SUMMARY OF THE INVENTION

The exemplary embodiments of the present invention have been made to solve the above problems, and provide a biosensor that acquires photoelectric pulse signals. The biosensor can reduce a pressing force exerted on a circuit board during measurement, prevent components mounted on the circuit board from causing connection errors or other defects, and reduce stray light received by the biosensor without passing through a living body.

An exemplary embodiment of the present invention provides a biosensor that includes a circuit board, a light emitting device and a light receiving device disposed on a main surface of the circuit board with a predetermined distance apart from each other, and a housing to which the circuit board is attached and including a pair of openings respectively corresponding to the light emitting device and the light receiving device. Moreover, the housing includes a light shield portion disposed at least between the pair of openings. The light shield portion (or simply "light shield") includes a light shield member that is disposed on a surface of the housing facing the circuit board, has a light shielding characteristics and flexibility, and is deformed by coming into contact with the circuit board when the circuit board is attached to the housing.

The biosensor according to the exemplary embodiment includes a housing to which the circuit board is attached and including a pair of openings respectively corresponding to the light emitting device and the light receiving device, with the housing including a light shield portion disposed at least between the pair of openings. The light shield portion includes a light shield member that is disposed on a surface of the housing facing the circuit board, has a light shielding characteristics and flexibility, and is deformed by coming into contact with the circuit board when the circuit board is attached to the housing. When the light shield member having flexibility is deformed by coming into contact with the circuit board, a gap can be prevented from being formed between the light shield portion and the circuit board, and stray light that is directly incident on the light receiving device from the light emitting device can be reliably blocked. The light shield member having flexibility can fully reduce pressure exerted on the circuit board. This structure can thus prevent electronic components mounted on the circuit board from causing connection errors or other defects. As such, this structure can advantageously prevent a pressing force exerted on the circuit board during measurement, prevent components mounted on the circuit board from causing connection errors or other defects, and reduce stray light received by the biosensor without passing through a living body.

DETAILED DESCRIPTION

Exemplary embodiments of the present invention will be described in detail, below, with reference to the drawings. Throughout the drawings, the same or like portions are denoted with the same reference signs. In each drawing, the same components are denoted with the same reference signs without being described redundantly. Here, a case where a biosensor according to the present invention is included in a holdable pulsimeter will be described by way of example.

Figure 1:
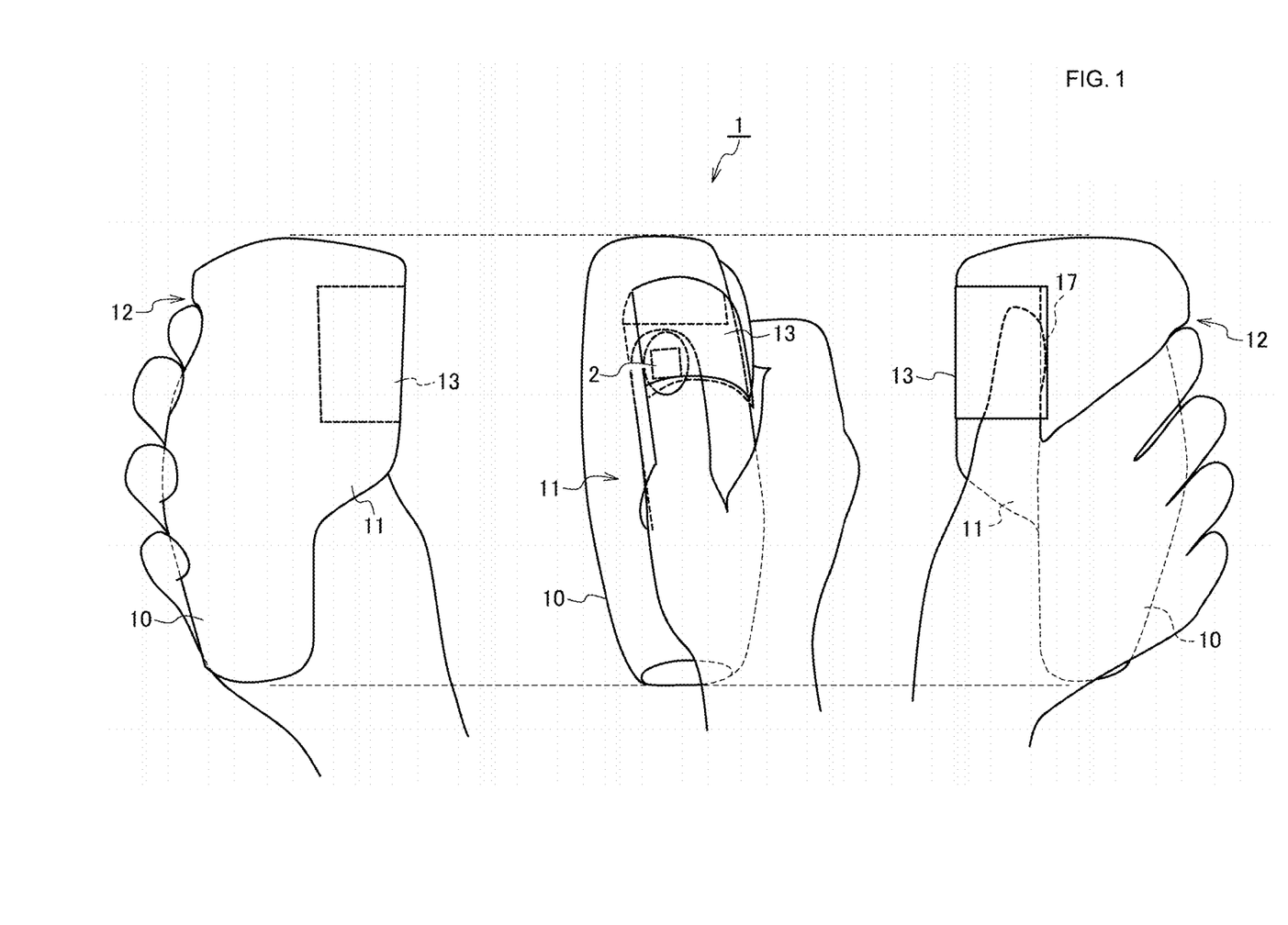
FIG. 1 includes a front view and left and right side views of the appearance of a holdable pulsimeter, which includes a biosensor according to an exemplary embodiment, and the state of the holdable pulsimeter while being held by a hand.
Figure 2:
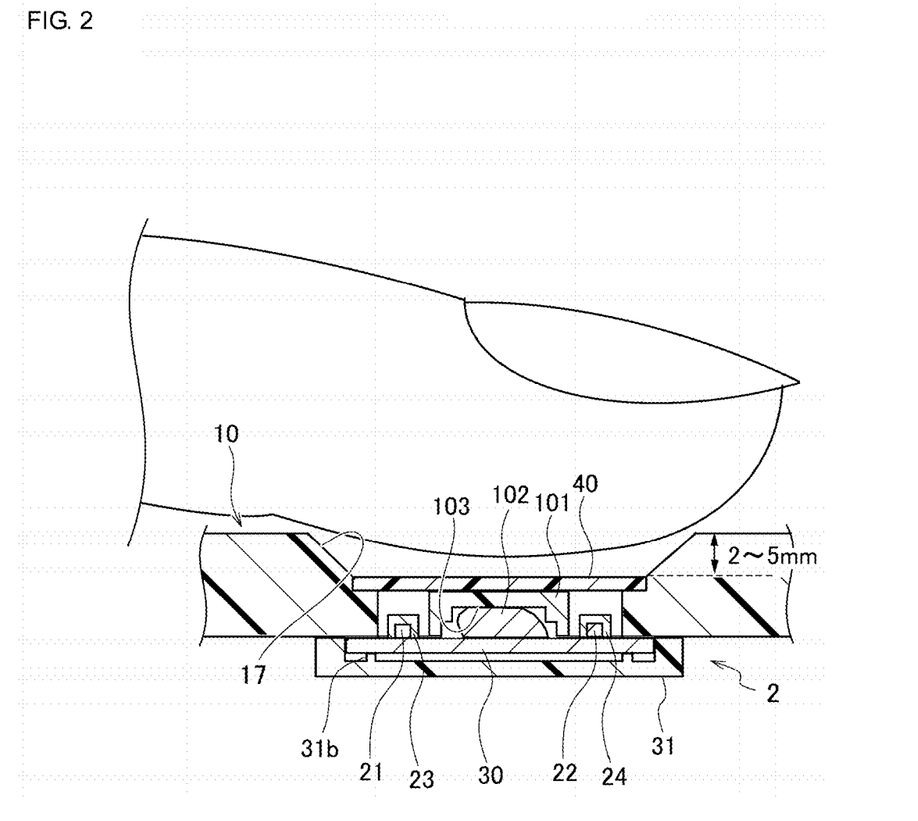
FIG. 2 is an enlarged cross-sectional view of a recess formed in the surface of the body of a holdable pulsimeter, which includes a biosensor according to an exemplary embodiment.
Figure 3:
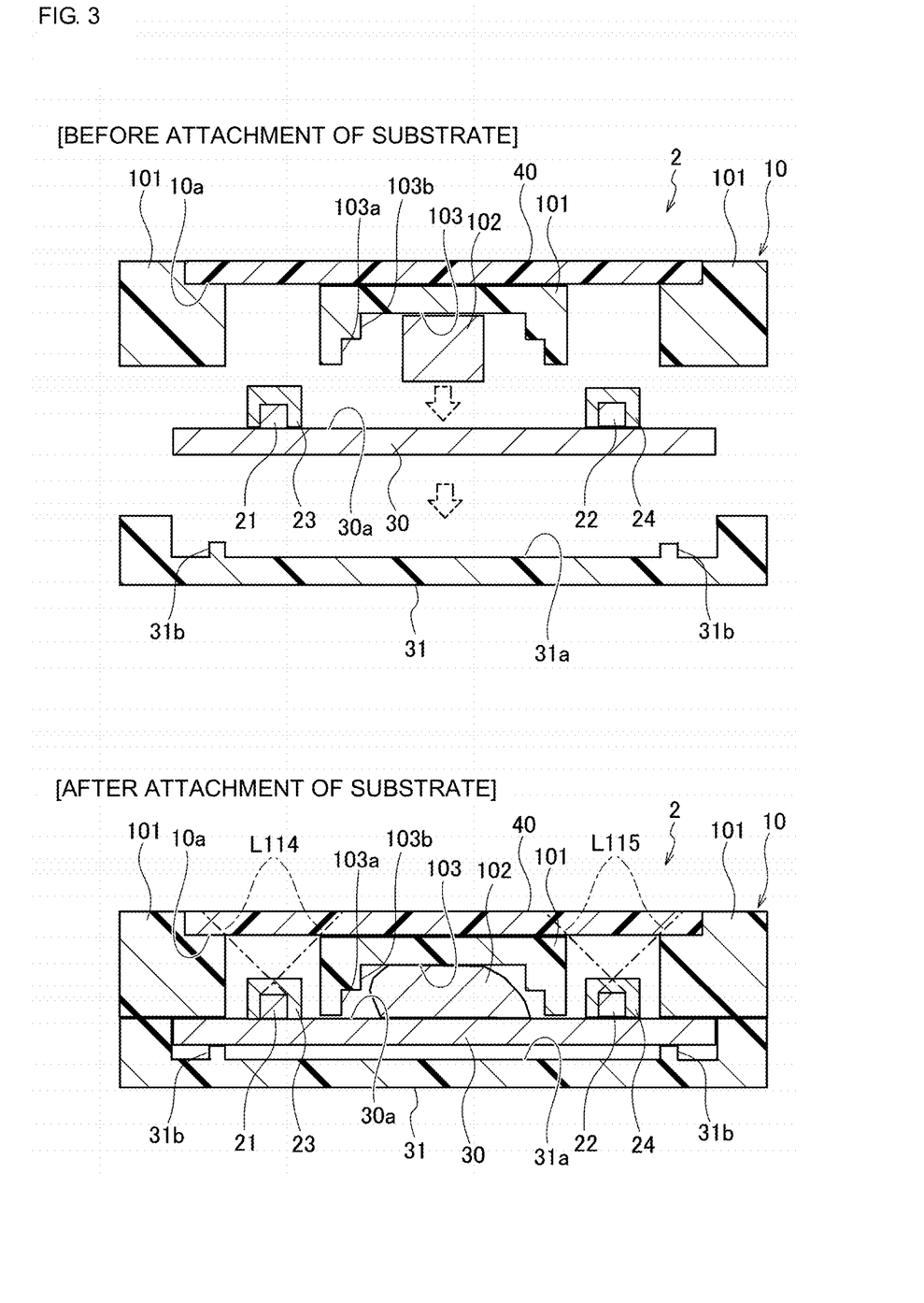
FIG. 3 includes vertical cross-sectional views of a biosensor according to an exemplary embodiment.
Figure 4:
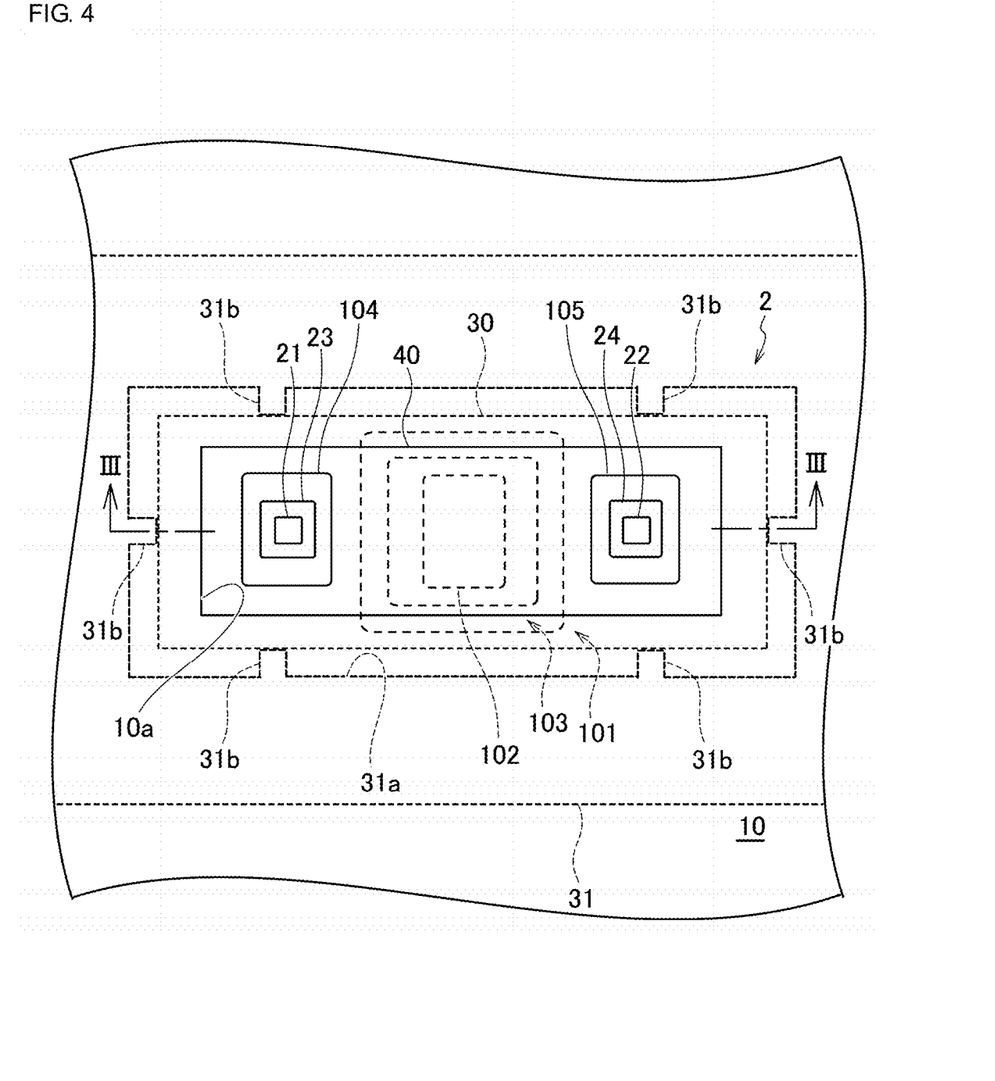
FIG. 4 is a plan view of a biosensor according to an exemplary embodiment.
Figure 5:
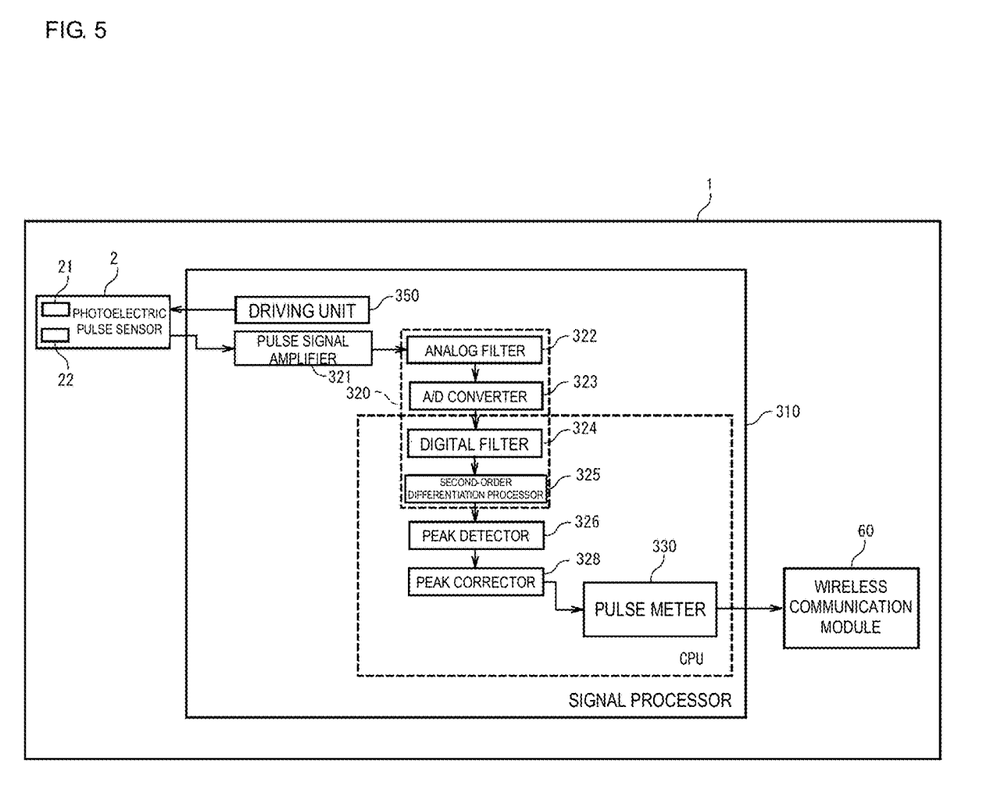
FIG. 5 is a functional block diagram of a holdable pulsimeter, which includes a biosensor according to an exemplary embodiment.

With reference to FIG. 1 to FIG. 5, a biosensor 2 according to an exemplary embodiment and a holdable pulsimeter 1 including the biosensor 2 will be described. FIG. 1 includes a front view and left and right side views of the appearance of the holdable pulsimeter 1, which includes the biosensor 2, and the state of the holdable pulsimeter 1 while being held by a hand. FIG. 2 is an enlarged cross-sectional view of a recess 17 formed in the surface of the body of the holdable pulsimeter 1. FIG. 3 includes vertical cross-sectional views of the biosensor 2 taken along line III-III of FIG. 4. Here, an upper portion is a cross-sectional view of a body 10 to which a circuit board 30 has not been attached, and a lower portion is a cross-sectional view of the body 10 to which the circuit board 30 has been attached. FIG. 4 is a plan view of the biosensor 2. FIG. 5 is a functional block diagram of the holdable pulsimeter 1, which includes the biosensor 2.

According to the exemplary embodiment, when held with a single hand of a user, the holdable pulsimeter 1 acquires a photoelectric pulse from the fingertip of the thumb of the user to measure the pulse rate or other vital signs.

The holdable pulsimeter 1 includes a body 10 (also referred to has a "housing") having a substantially rotatable ellipsoidal shape for a user to hold with the thumb and four fingers of the right or left hand during measurement. The body 10 includes a stopper portion 11 (also referred to as a "stopper"), which comes into contact with the side surfaces of the middle joint and basal joint of the thumb of the user holding the body 10 with a single hand to restrict the position of the thumb. The stopper portion 11 protrudes to extend in the axial direction of the body 10. The body 10 is preferably made of, for example, an opaque resin. Here, the phrase "the substantially rotatable ellipsoidal shape" is not limited to a rotatable ellipsoid strictly defined geometrically according to the exemplary embodiment.

As further shown, the body 10 includes a stepped portion 12, which guides the forefinger of the user to an appropriate holding position when the user is to hold the body 10, at a position closer to the tip than the center on the back surface when viewed from the stopper portion 11. Specifically, by placing the forefinger along the stepped portion 12 when the user is to hold the body 10, the position of each finger is substantially fixed to reduce the variance of the vertical position of the fingertip of the thumb, that is, the variance of the position of the fingertip relative to a photoelectric pulse sensor 2, described below.

The body 10 also has a light shielding cover 13 attached thereto. The light shielding cover 13 has a light shielding function to block external perturbation light from entering the photoelectric pulse sensor 2, described blow, during measurement. The light shielding cover 13 has a substantially semi-cylindrical shape to cover the upper portion of the photoelectric pulse sensor 2, described below, that is, to cover the thumb of a user during measurement.

The photoelectric pulse sensor 2 (generally referred to as a "biosensor") is disposed at a portion of the body 10 shifted from the stopper portion 11 in the circumferential direction of the body 10. The photoelectric pulse sensor 2 includes a light emitting device 21 and a light receiving device 22 to acquire photoelectric pulse signals from the fingertip of the thumb restrained by the stopper portion 11. The photoelectric pulse sensor 2 is a biosensor that optically detects photoelectric pulse signals using the light absorbing characteristics of the hemoglobin in the blood.

Here, the area of the body 10 in which the photoelectric pulse sensor 2 including the light emitting device 21 and the light receiving device 22 is disposed is set back into, for example, a substantially ellipsoid from the surrounding surface. Specifically, the photoelectric pulse sensor 2 is disposed at the center portion of the recess 17 formed in the body 10. Thus, the user can reliably place the fingertip of the thumb over the photoelectric pulse sensor 2 by bringing the inner surface of the thumb into contact with the recess 17 without visual observation. More specifically, as illustrated in FIG. 2, the recess 17 is preferably set back approximately 2 to 5 mm from the surface of the body 10 according to the exemplary embodiment.

The structure of the photoelectric pulse sensor 2 will now be described in detail. The circuit board 30 is, for example, a rectangular thin printed circuit board. More specifically, the circuit board 30 is, for example, a glass epoxy substrate including as a base a board of flame retardant type 4 (e.g., FR4) on which a wiring pattern made of, for example, copper foil is formed.

The light emitting device 21 and the light receiving device 22 are mounted on a main surface 30a of the rectangular circuit board 30 at a predetermined distance apart. The distance between the light emitting device 21 and the light receiving device 22 is, for example, approximately 4 to 20 mm. Preferably, a large electronic component is not disposed between the light emitting device 21 and the light receiving device 22 on the circuit board 30.

Examples usable as the light emitting device 21 include a LED, a vertical cavity surface emitting laser ("VCSEL"), and a resonant LED. Examples preferably usable as the light receiving device 22 include a photodiode and a phototransistor.

A light-emitting-device sealing portion 23, which encloses the light emitting device 21 therein, and a light-receiving-device sealing portion 24, which encloses the light receiving device 22 therein, are disposed on the main surface 30a of the circuit board 30. The light-emitting-device sealing portion 23 is formed, for example, in a columnar shape with a translucent resin to enclose the light emitting device 21 therein. Similarly, the light-receiving-device sealing portion 24 is formed, for example, in a columnar shape with a translucent resin to enclose the light receiving device 22 therein. Examples of a translucent resin used for the light-emitting-device sealing portion 23 and the light-receiving-device sealing portion 24 include a transparent epoxy resin. The light-emitting-device sealing portion 23 and the light-receiving-device sealing portion 24 may be formed into a rectangular parallelepiped.

The circuit board 30 on which the light emitting device 21 enclosed in the light-emitting-device sealing portion 23 and the light receiving device 22 enclosed in the light-receivingdevice sealing portion 24 are mounted is fitted into, for example, a rectangular recessed portion 31a formed in a plate-shaped substrate stopper 31. The substrate stopper 31 is fixed to the housing 10 made of, for example, an opaque resin, with screws or other devices from the inner side. Misalignment of the positions of the light emitting device 21 and the light receiving device 22 mounted on the circuit board 30 with respect to openings 104 and 105 in the housing 10 affects the sensor properties. Thus, the light emitting device 21 and the light receiving device 22 need to be fixed to have minimum misalignment. The tolerance of misalignment is determined based on, for example, the size of the light emitting device, the size of the light receiving device, the opening diameter, the thickness of the housing in which the openings 104 and 105 are formed, the characteristics of the light emitting device, and the characteristics of the light receiving device.

It should be appreciated that when, for example, an LED is used as the light emitting device 21, the light emitting device 21 is affected by vertical misalignment further than lateral misalignment. Thus, the sensor 2 needs to be designed and configured to not allow a light shield member 102, described below, to be interposed between the housing 10 and the circuit board 30. The profile of the circuit board 30 is desirably used to prevent lateral misalignment. More specifically, for example, in the present embodiment, multiple positioning protrusions 31b are disposed on the inner circumference and the bottom portion of the rectangular recessed portion 31a of the substrate stopper 31 into which the circuit board 30 is fitted. The multiple protrusions 31b fix the position of the circuit board 30 relative to the housing 10. Alternatively, for example, a positioning through-hole may be formed in the circuit board 30, and a pin disposed on the housing 10 or the substrate stopper 31 may be inserted into the positioning hole of the circuit board 30 to fix the position of the circuit board 30.

According to an exemplary aspect, the substrate stopper 31 is desirably fixed to the housing 10 with a screw or the like, but instead of the above fixing method, the substrate stopper 31 may be fixed with, for example, a tape or adhesive. A through-hole may be formed in the circuit board 30 and a screw hole may be formed in the housing 10 to directly fix the circuit board 30 with a screw, or the housing 10 may have such a shape as to allow the circuit board 30 to be fitted thereto to fix the circuit board 30. Alternatively, the circuit board 30 may be fixed with a tape or adhesive. However, to directly fix the circuit board 30 with a screw, attention should be paid not to cause stress, which easily occurs at the screwed portion of the circuit board 30 and easily distorts the circuit board 30. The structure illustrated in FIG. 3 may be removable from the housing 10, and the circuit board 30 fixed to the substrate stopper 31 and the surrounding portions of the openings 104 and 105 can be attached to the housing 10. The measurement performance of the photoelectric pulse sensor 2 is affected by assembly errors of the housing 10 to the openings 104 and 105. However, the performance assessment is difficult to perform after the circuit board 30 is installed in the substantially rotational ellipsoidal housing 10. Thus, only the surrounding portions of the openings 104 and 105 of the housing 10 may be designed detachable to facilitate the performance assessment. In either method, the circuit board 30 needs to be fixed to the housing 10 not to move even when receiving, for example, vibrations. This is because movement of the circuit board 30 relative to the housing 10 changes the received amount of light, and serves as a noise to adversely affect the measurement. If the circuit board 30 would be fixed at many positions or over a wide area of the housing 10 that is warped, the circuit board 30 may be distorted when fixed, and the components mounted on the circuit board 30 may have problems of connection errors or other defects. Such a problem should be taken into consideration in designing the sensor 2.

As described above, the housing 10 has the opening 104 formed so that the axis of the light emitting device 21 is aligned with the axis of the opening 104 when the circuit board 30 is attached to the housing 10. Similarly, the housing 10 has the opening 105 formed so that the axis of the light receiving device 22 is aligned with the axis of the opening 105. Specifically, the pair of openings 104 and 105 respectively correspond to the light emitting device 21 and the light receiving device 22. Thus, the circuit board 30 is fixed to the housing 10 while having the portion on which the light emitting device 21 and the light receiving device 22 mounted facing to the outer side of the housing 10. Through the openings 104 and 105 of the housing 10 respectively corresponding to the light emitting device 21 and the light receiving device 22, light is emitted to the outside of the housing 10 from the light emitting device 21, and light returned after being dispersed or reflected is received by the light receiving device 22.

The housing 10 includes a light shield portion 101 (or simply a "light shield"), disposed adjacent to the pair of openings 104 and 105 and between the pair of openings 104 and 105 when viewed in a direction perpendicular to the circuit board 30. Specifically, when the circuit board 30 is assembled, the light shield portion 101 is disposed adjacent to the light emitting device 21 and the light receiving device 22 and between the light emitting device 21 and the light receiving device 22. The light shield portion may be disposed only between the pair of openings 104 and 105, that is, only between the light emitting device 21 and the light receiving device 22. Moreover, a material such as epoxy resin containing powder with light shielding characteristics such as carbon black is preferably usable as the light shield portion 101.

According to the exemplary embodiment, the light shield portion 101 includes a recessed portion 103 on the surface facing the circuit board 30 at least between the light emitting device 21 and the light receiving device 22. Particularly, the recessed portion 103 of the light shield portion 101 has a shape having two steps from the opening toward the bottom. Specifically, a wide and shallow first recessed portion 103a is firstly formed in the light shield portion 101, and a narrow and deep second recessed portion 103b is formed in the first recessed portion 103a.

A light shield member 102 having flexibility or elasticity is disposed in the second recessed portion 103b. For example, the second recessed portion 103b may be tapered instead of having a stepped shape. The second recessed portion 103b has a size larger than the light shield member 102 to allow for misalignment of the position of the light shield member 102 so that light shield member 102 is reliably disposed in the second recessed portion 103b.

The peripheral portion of the light shield portion 101, that is, the outer edge portion of the first recessed portion 103a is kept away from the circuit board 30 when the circuit board 30 is attached to the housing 10. For example, if the peripheral portion of the light shield portion 101 comes into contact with the circuit board 30, the circuit board 30 may bear stress, and electronic components mounted on the circuit board 30 may cause connection errors or other defects. This structure is made to avoid such problems.

An end portion of the light shield member 102 that has light shielding characteristics and flexibility is attached to the light shield portion 101, specifically, to the bottom portion of the second recessed portion 103b. When the circuit board 30 is attached to the housing, the light shield member 102 is deformed by coming into contact with the circuit board 30 (specifically, fills the gap between the circuit board 30 and the light shield portion 101 to block light). The light shield portion 101 and the light shield member 102 may be formed of an integrated body or separate bodies. According to the exemplary embodiment, the recessed portion 103 and the light shield member 102 may be disposed adjacent to the light emitting device 21 and/or the light receiving device 22 besides between the light emitting device 21 and the light receiving device 22.

Examples usable as the material of the light shield member 102 include foamed plastic, rubber, resin, and metal having a spring mechanism. The light shield member 102 preferably has a shape of, for example, a quadrangular prism, but may have another shape as long as it is configured to block light from the light emitting device 21 from directly arriving at the light receiving device 22, for example, a shape of a hollow tube or a bag. With no external force exerted, the light shield member 102 has a dimension in the depth direction of the recessed portion 103 slightly larger than the depth of the recessed portion 103. As described above, the light shield member 102 is designed to be deformed by coming into contact with the surface of the circuit board 30 when the circuit board 30 on which the light emitting device 21 and the light receiving device 22 are mounted is fixed to the housing 10. When formed from a material having low flexibility or designed to be deformed a large amount when the circuit board 30 is fixed, the light shield member 102 exerts large stress on the circuit board 30, and the components mounted on the circuit board 30 may cause connection errors or other defects. Thus, preferably, the light shield member 102 is formed from a material having relatively large flexibility or designed to be deformed a lesser amount. The light shield member 102 may be attached to the second recessed portion 103b by, for example, being bonded with a double-sided tape or fixed with an adhesive. Alternatively, the light shield member 102 may be fitted to the housing 10.

As described above, preferably, the inner size of the first recessed portion 103a is larger than an area that can expand laterally, or along the substrate surface, with deformation of the light shield member 102 when the circuit board 30 is fixed. Specifically, for example, when a sponge is used as the light shield member 102, the sponge may be obliquely squashed depending on the pressure direction. Thus, the inner size of the first recessed portion 103a is determined to prevent an end portion of the squashed sponge from being held between the peripheral portion of the light shield portion 101, specifically, the outer edge portion of the first recessed portion 103a, and the circuit board 30.

As further shown, a translucent cover 40 is attached to the outer surface of the housing 10, and specifically, the upper surface of the light shield portion 101 to cover the openings 104 and 105. According to the exemplary embodiment, the cover 40 is disposed parallel to the circuit board 30 with the light shield portion 101 interposed therebetween. The cover 40 is, for example, a flat plate member made of a material such as translucent acryl, polycarbonate, or polyethylene terephthalate (PET) with a thickness of approximately 0.1 to 2 mm. The cover 40 may be integrated with the housing 10. In an exemplary aspect, the opening 104 for the light emitting device 21 and the opening 105 for the light receiving device 22 can be covered with different translucent covers. However, because the opening 104 for the light emitting device 21 and the opening 105 for the light receiving device 22 are usually spaced only a short distance apart from each other, covering the openings with different translucent covers may be difficult in terms of design or manufacture.

Preferably, the cover 40 is installed on the outer side of the openings 104 and 105 and is fixed to a recessed portion 10a on the outer side of the housing 10 by, for example, fitting, bonding, or adhering. The cover 40 thus fixed has a structure that can bear the external pressure. Specifically, the cover 40 can be prevented from being detached from the openings 104 and 105 or pressed into the openings 104 and 105 with an external pressure.

The cover 40 covers the two openings 104 and 105 formed in the housing 10 to prevent, for example, water, sweat, or dust from entering the inside of the sensor through the openings 104 and 105 and causing defects in the sensor.

The end portion of the cover 40 closer to the light emitting device 21 is located on the outer side of the opening 104. Specifically, the end portion of the cover 40 is disposed so as not to overlap the opening 104 when viewed in a direction normal to the main surface 30a of the circuit board 30. Particularly, the cover 40 is disposed to cover an area wider than the opening 104 so that the side surface of the end portion does not cross all virtual lines L114 passing through the entire peripheral portion of the light emitting area of the light emitting device 21 and the entire peripheral portion of the opening 104 of the housing 10. In other words, the opening 104 is formed so that all the virtual lines L114 that pass through the light emitting area of a light emitter of the light emitting device 21 and the entire inner peripheral portion at the opening edge of the opening 104 of the housing 10 around the light emitting device 21 do not cross the side surface of the end portion of the cover 40.

Similarly, the end portion of the cover 40 closer to the light receiving device 22 is located on the outer side of the opening 105. Specifically, the end portion of the cover 40 is disposed so as not to overlap the opening 105 when viewed in a direction normal to the main surface 30a of the circuit board 30. Particularly, the cover 40 is disposed to cover an area wider than the opening 105 so that the side surface of the end portion does not cross all virtual lines L115 passing through the entire peripheral portion of the light receiving area of the light receiving device 22 and the entire peripheral portion of the opening 105 of the housing 10. In other words, the opening 105 is formed so that all the virtual lines L115 that pass through the light receiving area of a light receiver of light receiving device 22 and the entire inner peripheral portion at the opening edge of the opening 105 of the housing 10 around the light receiving device 22 do not cross the side surface of the end portion of the cover 40.

The photoelectric pulse sensor 2 having the above structure detects photoelectric pulses by allowing a portion of the living body, for example, the fingertip of the thumb of the right hand of an examinee to come into contact with the photoelectric pulse sensor 2.

To detect photoelectric pulses, light emitted from the light emitting device 21 passes through the light-emitting-device sealing portion 23, is incident on the cover 40 through the opening 104, and is incident on the fingertip through the cover 40.

The light that has been incident on and has passed through the fingertip passes through the cover 40, and enters the opening 105. The light then passes through the light-receiving-device sealing portion 24, and is received by the light receiving device 22. Thus, the change of intensity of light that has passed through the fingertip is acquired in the form of a photoelectric pulse signal.

More specifically, as illustrated in FIG. 5, the light emitting device 21 emits light in accordance with a pulse-form driving signal output from a driving unit 350 of a signal processor 310, described later. The driving unit 350 generates and outputs pulse-form driving signals that drive the light emitting device 21.

The light receiving device 22 outputs a detection signal corresponding to the intensity of light that has been emitted from the light emitting device 21 and that has passed through the thumb or has been incident thereon after being reflected off the thumb.

The light receiving device 22 is connected to the signal processor 310, and the photoelectric pulse signal acquired by the light receiving device 22 is output to the signal processor 310. The signal processor 310 processes the input photoelectric pulse signal to measure, for example, the pulse rate or pulse interval.

Here, the body 10 accommodates the signal processor 310 and a wireless communication module 60, which transmits vital signs, such as the measured photoelectric pulse signals or pulse rate, to external devices. The body 10 also accommodates a battery that feeds power to, for example, the photoelectric pulse sensor 2, the signal processor 310, and the wireless communication module 60.

The signal processor 310 includes, an amplifier 321, a signal processor 320, a peak detector 326, a peak corrector 328, and a pulse meter 330. The signal processor 320 includes an analog filter 322, an A/D converter 323, a digital filter 324, and a second-order differentiation processor 325.

Among the above components, the digital filter 324, the second-order differentiation processor 325, the peak detector 326, the peak corrector 328, and the pulse meter 330 can comprise one or more CPUs that are configured to perform the computations described herein, a ROM that stores data or programs causing the CPU to execute various processes, and a RAM that temporarily stores various data such as computation results. Specifically, when the programs stored in the ROM are executed by the CPU, the functions of the above components are executed.

The amplifier 321 is formed from, for example, an operational amplifier, to amplify the photoelectric pulse signal detected by the photoelectric pulse sensor 2. The photoelectric pulse signal amplified by the amplifier 321 is output to the signal processor 320.

As described above, the signal processor 320 includes the analog filter 322, the A/D converter 323, the digital filter 324, and the second-order differentiation processor 325. The signal processor 320 performs filtering and second-order differentiation on the photoelectric pulse signal amplified by the amplifier 321 to extract the pulsation component.

The analog filter 322 and the digital filter 324 are configured to perform filtering to remove components other than the frequency characterizing the photoelectric pulse signal, specifically, remove noise to improve S/N. More specifically, in the photoelectric pulse signal, the frequency component around zero point one (0.1) to several ten hertz is dominant. Thus, the analog filter 322 and the digital filter 324 formed of, for example, a low-pass filter or a band-pass filter are used for filtering to selectively allow only signals in the above frequency range to pass therethrough to improve S/N.

To only extract the pulsation component, specifically, when properties such as the waveform are not required, the passage frequency range may be further narrowed to block the component other than the pulsation component to improve noise immunity. Instead of providing both the analog filter 322 and the digital filter 324, only one of the analog filter 322 and the digital filter 324 may be disposed. The photoelectric pulse signal subjected to filtering by the analog filter 322 and the digital filter 324 is output to the second-order differentiation processor 325.

The second-order differentiation processor 325 acquires the second-order differentiation pulse wave (hereinafter referred to as "an accelerated pulse wave") by subjecting the photoelectric pulse signal to second-order differentiation. The acquired accelerated pulse wave is output to the peak detector 326. The pulse rise point of the photoelectric pulse has no clear change and may be difficult to detect. Thus, the photoelectric pulse signal is preferably converted into the accelerated pulse wave for peak detection. However, the second-order differentiation processor 325 is not necessary and may be omitted.

The peak detector 326 detects the peak of the photoelectric pulse signal (e.g., an accelerated pulse wave) subjected to filtering by the signal processor 320. The peak detector 326 performs peak detection within a normal range of the pulse interval, and stores, in a RAM or another storage, information such as peak time or a peak amplitude for each of all the detected peaks.

The peak corrector 328 calculates the latency of the photoelectric pulse signal in the signal processor 320. The peak corrector 328 corrects the peak of the photoelectric pulse signal (e.g., the accelerated pulse wave) detected by the peak detector 326 based on the latency of the calculated photoelectric pulse signal. The peak of the corrected accelerated pulse wave is output to the pulse meter 330.

The pulse meter 330 is configured to calculate the pulse rate from the peak interval of the accelerated pulse wave corrected by the peak corrector 328. The pulse meter 330 also is configured to calculate properties such as the pulse interval or the change ratio of the pulse interval.

The measurement data such as the acquired pulse rate, pulse interval, or change ratio of the pulse interval is transmitted to, for example, a PC or a mobile music player or a smartphone including a display via the wireless communication module 60. Here, data of, for example, measured date and time is also preferably transmitted in addition to the measurement result or the detection result.

Now, a usage of the holdable pulsimeter 1 will be described. The holdable pulsimeter 1 is used to detect a photoelectric pulse signal. To measure the pulse rate or other properties, as illustrated in FIG. 1, a user grips the holdable pulsimeter 1 with the thumb and the four fingers of the right hand.

When a user holds the body 10, the user moves the thumb until it hits the stopper portion 11, specifically, from the right to the left in the example in FIG. 1 to bring the inner surface of the thumb over the recess 17 to bring the fingertip of the thumb into contact with the photoelectric pulse sensor 2.

Thus, the photoelectric pulse sensor 2 acquires a photoelectric pulse signal from the fingertip of the thumb. The signal processor 310 thus measures the properties such as the pulse rate. The method for measuring the pulse rate or other properties is the same as described above, and will not be described in detail, here.

Thus, the properties such as the photoelectric pulse signal or pulse rate can be detected or measured by a user holding the holdable pulsimeter 1. Information of the properties such as the detected or measured photoelectric pulse signal or pulse rate is transmitted to external devices by the wireless communication module 60.

As described above in detail, the present embodiment includes the housing 10 to which the circuit board 30 is attached. The housing 10 includes the pair of openings 104 and 105 respectively corresponding to the light emitting device 21 and the light receiving device 22, and the light shield portion 101 disposed at least between the pair of openings 104 and 105. The light shield portion 101 includes the light shield member 102. The light shield member 102 is disposed on the surface of the housing 10 facing the circuit board 30, has a light shielding characteristics and flexibility, and is deformed when coming into contact with the circuit board 30 when the circuit board 30 is attached to the housing 10. Since the light shield member 102 having flexibility is deformed by coming into contact with the circuit board 30, a gap is prevented from being formed between the light shield portion 101 and the circuit board 30 to reliably block stray light that is directly incident on the light receiving device 22 from the light emitting device 21. The light shield member 102 having flexibility can fully reduce the pressure exerted on the circuit board 30. Thus, the electronic components mounted on the circuit board 30 can be prevented from causing connection errors or other defects. Thus, the pressing force exerted on the circuit board during measurement can be reduced, the components mounted on the circuit board 30 can be prevented from causing connection errors or other defects, and stray light received without passing through a living body can be reduced. A light shielding structure can be achieved relatively easily with a reasonable cost.

According to the exemplary embodiment, the recessed portion 103 is formed on the surface of the light shield portion 101 facing the circuit board 30 at least between the light emitting device 21 and the light receiving device 22. The light shield member 102 is disposed at the bottom portion of the recessed portion 103 in the housing 10. When the circuit board 30 is attached to the housing 10, the peripheral portion of the recessed portion 103 is kept apart from the circuit board 30. Thus, when the light shield member 102 having flexibility is deformed by coming into contact with the circuit board 30, a gap is formed between the housing 10 and the circuit board 30 by, for example, part of the light shield member 102 being held between the housing 10 and the circuit board 30, so that the dimension in the height direction is prevented from being changed, which prevents deterioration in measurement accuracy due to a change in the dimension in the height direction. When a relatively large external force is exerted, the peripheral portion of the recessed portion 103 comes into contact with the circuit board 30 to prevent components including the light shield portion 101 from being further deformed, so that the sensor 2 can be prevented from being broken.

In the exemplary embodiment, the recessed portion 103 formed in the light shield portion 101 has a shape having two steps from the opening toward the bottom portion. Thus, when the light shield member 102 having flexibility is deformed by coming into contact with the circuit board 30, for example, part of the light shield member 102 is further reliably prevented from being held between the housing 10 and the circuit board 30. When part of the light shield member 102 is held between the housing 10 and the circuit board 30, a gap is formed between the housing 10 and the circuit board 30 and prevents the dimension in the height direction from being changed, and thus can further reliably prevent deterioration of measurement accuracy due to a change of the dimension in the height direction.

The exemplary embodiment includes the translucent cover 40 disposed to cover the openings 104 and 105 of the housing 10. The openings 104 and 105 of the housing 10 is thus covered with the translucent cover 40 to prevent, for example, water or dust from relatively easily entering the inside of the housing 10 and causing defects. This structure can bear external pressure.

In the exemplary embodiment, the openings 104 and 105 are formed so that all the virtual lines L114 that pass through the entire peripheral portion of the light emitting area of the light emitting device 21 and the entire peripheral portion of the opening 104 of the housing 10 around the light emitting device 21 do not cross the side surface of the end portion of the cover 40, and so that all the virtual lines L115 that pass through the entire peripheral portion of the light receiving area of the light receiving device 22 and the entire peripheral portion of the opening 105 of the housing 10 around the light receiving device 22 do not cross the side surface of the end portion of the cover 40. Thus, light emitted from the light emitting device 21 is less easily incident on the end portion of the cover 40. Moreover, stray light reflected off the end portion of the cover 40 is less easily incident on the light receiving device 22. Thus, stray light that is transmitted through the cover 40 and received without passing through a living body can be more effectively reduced.

According to the exemplary embodiment, the area of the housing 10 in which the light emitting device 21 and the light receiving device 22 are disposed is set back from the surrounding surface. Thus, for example, by bringing the inner surface of the fingertip over the recess, the fingertip can be reliably placed over the photoelectric pulse sensor 2 without visual observation. Particularly, the user perceives by touch the position at which the fingertip is to be placed. Thus, misalignment of the fingertip in the lateral direction and the vertical direction can be reduced, so that a stable measurement can be performed. During measurement of, for example, the fingertip of the thumb, a user may become tired of continuously stretching the first joint of the thumb for a long time. However, the photoelectric pulse sensor 2 set back from the surrounding surface allows the thumb to be bent as appropriate to prevent the user from becoming tired.

It is noted that the exemplary embodiments of the present invention are not limited to the above embodiments, and may be changed into various different modifications. For example, in the embodiment, a photoelectric pulse sensor is used as an example of a biosensor. Instead of the photoelectric pulse sensor, the biosensor may be, for example, a proximity sensor, an oxygen saturation sensor, a blood flow sensor, or a spectral sensor.

In the above exemplary embodiment, the recessed portion 103 formed in the light shield portion 101 has a shape having two steps from the opening toward the bottom portion. Instead of the shape including two steps, the recessed portion 103 may have a shape including one step or three or more steps an alternative aspects.

In the above exemplary embodiment, the light shield member 102 is disposed between the light emitting device 21 and the light receiving device 22. However, the light shield member 102 may be disposed adjacent to the light emitting device 21 and/or the light receiving device 22.

In the above embodiment, the light shielding cover 13 is fixed, but the light shielding cover 13 may be swingable.

REFERENCE SIGNS LIST 1 holdable pulsimeter
2 photoelectric pulse sensor
10 body
101 light shield portion 102 light shield member
103, 103a, 103b recessed portion
104, 105 opening
11 stopper portion
12 stepped portion
13 light shielding cover
17 recess
21 light emitting device
22 light receiving device
23 light-emitting-device sealing portion
24 light-receiving-device sealing portion
30 circuit board
31 substrate stopper
31b protrusion
40 cover
60 wireless communication module
L114, L115 virtual line

The invention claimed is:

1. A biosensor, comprising:
a circuit board;
a light emitting device and a light receiving device disposed on a main surface of the circuit board and spaced a distance apart from each other; and
a housing attached to the circuit board and that includes a pair of openings that correspond to the light emitting and receiving devices, respectively, with the housing including a light shield disposed at least between the pair of openings,
wherein the light shield includes a flexible light shield member with light shielding characteristics, and
wherein the flexible light shield member is deformable and is disposed on a surface of the housing facing the circuit board.

2. The biosensor according to claim 1,
wherein the light shield includes a recessed portion on a surface of the housing that faces the circuit board at least between the light emitting device and the light receiving device, and
wherein the light shield member is disposed on a bottom portion of the recessed portion.

3. The biosensor according to claim 2, wherein the recessed portion includes a peripheral portion that is kept apart from the circuit board when the circuit board is attached to the housing.

4. The biosensor according to claim 3, wherein the recessed portion of the light shield has a shape that includes a plurality of steps from an opening to the bottom portion of the recessed portion.

5. The biosensor according to claim 4, wherein the plurality of steps extend outwardly in a peripheral direction as the recessed portion extends towards the circuit board.

6. The biosensor according to claim 4, wherein the flexible light shield member is disposed in the recessed portion with a gap provided between the flexible light shield member and at least a portion of the plurality of steps.

7. The biosensor according to claim 4, wherein a portion of the plurality of steps is disposed in a lateral direction between the light emitting device and the light receiving device.

8. The biosensor according to claim 7, wherein a step of the plurality of steps that extends inward towards the flexible light shield member is disposed in the lateral direction between the light emitting device and the light receiving device.

9. The biosensor according to claim 1, further comprising a translucent member disposed to cover the pair of openings formed in the housing.

10. The biosensor according to claim 9, wherein the translucent member is a cover having a plate shape and is disposed parallel to the circuit board with the light shield interposed therebetween.

11. The biosensor according to claim 10,
wherein the housing is configured such that all virtual lines that pass through an entire peripheral portion of a light emitting area of the light emitting device and an entire peripheral portion of the opening of the housing around the light emitting device do not cross a side surface of an end portion of the cover, and
wherein the housing is configured such that all virtual lines that pass through an entire peripheral portion of a light receiving area of the light receiving device and an entire peripheral portion of the opening of the housing around the light receiving device do not cross the side surface of the end portion of the cover.

12. The biosensor according to claim 11, wherein the side surface of the end portion of the cover extends outward of the respective entire peripheral portions of the light emitting area and the light receiving area in a direction normal to the main surface of the circuit board.

13. The biosensor according to claim 1, wherein an area of the housing on which the light emitting device and the light receiving device are mounted is set back from a surrounding area thereof.

14. The biosensor according to claim 1, wherein a gap is formed adjacent the flexible light shield member and between the housing and the circuit board when the circuit board is attached to the housing.

15. The biosensor according to claim 1, wherein the light shield member comprises at least one of a foamed plastic, rubber, resin, and a metal spring.

16. The biosensor according to claim 15, wherein the light shield member is coupled to the housing by one of a double-sided tape or an adhesive.

17. A biosensor comprising:
a circuit board having light emitting and receiving devices disposed thereon with a space therebetween; and
a housing configured to be attached to the circuit board and including a pair of openings extending over the light emitting and receiving devices, respectively, when the circuit board is attached to the housing,
wherein the housing includes a light shield disposed between the pair of openings and includes a recess that faces the circuit board at the space between the light emitting and receiving devices, and
wherein a flexible and deformable light shield member is disposed on a surface in the recess of the housing and facing the circuit board.

18. The biosensor according to claim 17, wherein the recess of the light shield includes a plurality of steps from an opening to a bottom of the recess opposite the circuit board.

19. The biosensor according to claim 18, wherein the plurality of steps extend outwardly in a peripheral direction as the recess extends towards the circuit board.

20. The biosensor according to claim 17, further comprising a translucent member disposed to cover the pair of openings in the housing.

21. The biosensor according to claim 20, wherein the translucent member is a cover having a plate shape and is disposed parallel to the circuit board with the light shield interposed therebetween.

22. The biosensor according to claim 21,
wherein the housing is configured such that all virtual lines that pass through an entire peripheral portion of a light emitting area of the light emitting device and an entire peripheral portion of the opening of the housing around the light emitting device do not cross a side surface of an end portion of the cover, and wherein the housing is configured such that all virtual lines that pass through an entire peripheral portion of a light receiving area of the light receiving device and an entire peripheral portion of the opening of the housing around the light receiving device do not cross the side surface of the end portion of the cover.

* * * * *